(12) United States Patent
Christy

(10) Patent No.: US 6,692,032 B2
(45) Date of Patent: Feb. 17, 2004

(54) MOLE MONITORING SYSTEM

(76) Inventor: Melanie Ann Christy, 5022 W. 86th Pl., Crown Point, IN (US) 46307

( * ) Notice: Subject to any disclaimer, the term of this patent is extended or adjusted under 35 U.S.C. 154(b) by 0 days.

(21) Appl. No.: 09/995,521

(22) Filed: Nov. 28, 2001

(65) Prior Publication Data

US 2003/0098580 A1 May 29, 2003

(51) Int. Cl.$^7$ .......................... B42D 11/00; B42D 15/00
(52) U.S. Cl. .................. 283/115; 283/63; 283/117; 283/900; 128/63; 128/736; 128/897; 600/300; 434/88; 434/262; 434/263; 434/267; 434/295; 602/42; 33/483
(58) Field of Search ..................... 283/62, 115, 117, 283/900; 128/897, 63, 736; 600/300; 434/88, 262, 263, 267, 295; 602/42; 33/483

(56) References Cited

U.S. PATENT DOCUMENTS

| | | | | |
|---|---|---|---|---|
| 2,557,428 A | * | 6/1951 | Grostic | 33/1 C |
| 4,131,998 A | * | 1/1979 | Spears | 33/1 BB |
| 4,328,051 A | * | 5/1982 | Robinette | 156/62 |
| 4,524,778 A | * | 6/1985 | Brown et al. | 600/549 |
| 5,018,531 A | * | 5/1991 | Hartman | 600/587 |
| 5,265,605 A | * | 11/1993 | Afflerbach | 600/300 |
| 5,605,165 A | * | 2/1997 | Sessions et al. | 128/888 |
| 5,636,873 A | * | 6/1997 | Sonsteby | 283/117 |
| 5,743,730 A | * | 4/1998 | Clester et al. | 433/26 |
| 6,155,603 A | * | 12/2000 | Fox | 283/115 |
| 6,168,438 B1 | * | 1/2001 | Leonard et al. | 434/81 |
| 6,412,491 B1 | * | 7/2002 | Rusin | 128/897 |
| 6,427,022 B1 | * | 7/2002 | Craine et al. | 128/922 |
| 6,568,938 B1 | * | 5/2003 | Prince et al. | 434/90 |
| 2002/0056459 A1 | * | 5/2002 | Rusin | 128/897 |

* cited by examiner

Primary Examiner—A. L. Wellington
Assistant Examiner—Mark T. Henderson
(74) Attorney, Agent, or Firm—Hartman & Hartman P.C.

(57) ABSTRACT

The present invention is a nontechnical, nonmechanical, easy to use, healthcare product that allows any individual to monitor changes in moles, freckles, or other skin growths in the comfort of their own home. It doubles as a record-keeping system that allows a person to compare new measures to their previously recorded measures—notice a change has occurred—and make a potentially life-saving appointment with a dermatologist. By using the flexible transparent sheets and a numeric value system, the product identifies changes in size, shape, color, "geography" of the mole and if any bleeding has occurred; all of which are important features in the development of skin cancer or melanoma. This product does not diagnose or treat a disease, but most importantly it provides people with a means of discovering a potential problem that normally would be undetected by the naked eye. This product has the potential to decrease medical care costs, reduce human suffering, and save lives.

9 Claims, 4 Drawing Sheets

| | |
|---|---|
| NAME: | 0-WHITE  3-BROWN  6-FLAT |
| | 1-TAN      4-BLUE      7-RAISED |
| LOCATION: | 2-RED      5-BLACK    8-BLOOD |
| DATE | TRACING AREA | APPEARANCE |
| | | 0  1  2  3  4  5  6  7  8 |
| | | 0  1  2  3  4  5  6  7  8 |
| | | 0  1  2  3  4  5  6  7  8 |
| | | 0  1  2  3  4  5  6  7  8 |
| ©2001 | | NOT A SUBSTITUTE FOR A PHYSICIAN. SEE A DERMATOLOGIST FOR REGULAR CHECKUPS. |

FIG. 1

| | | |
|---|---|---|
| 2.~ NAME: *John Doe* ~12. | | 0-WHITE 3-BROWN 6-FLAT |
| 3.~ LOCATION: *left knee* ~13. | | 1-TAN 4-BLUE 7-RAISED ~7.<br>2-RED 5-BLACK 8-BLOOD |
| 4.~ DATE | TRACING AREA ~6. | APPEARANCE ~8. |
| 5.~ ,14.<br>*6-15-99* | 15.~ ● | 0 ①  2 3 4 5 ⑥ 7 8 ~9.<br>  ~16.       ~17. |
| ,18.<br>*2-10-00* | 19.~ ● | 0 ① ② 3 4 5 ⑥ 7 8<br>        ~20. |
| ,21.<br>*12-30-00* | 22.~ ● | ,24.<br>0 ① ② 3 4 ⑤ 6 ⑦ 8<br>         ~23. |
| | | 0 1 2 3 4 5 6 7 8 |
| 11.~ ©2001 | | NOT A SUBSTITUTE FOR A PHYSICIAN.<br>SEE A DERMATOLOGIST<br>FOR REGULAR CHECKUPS. ~10. |

FIG.2

|  |  |
|---|---|
| NAME:<br><br>LOCATION: | 0-WHITE  3-BROWN  6-FLAT<br>1-TAN      4-BLUE      7-RAISED<br>2-RED      5-BLACK    8-BLOOD |
| DATE | TRACING AREA | APPEARANCE |
|  |  | 0 1 2 3 4 5 6 7 8 |
|  |  | 0 1 2 3 4 5 6 7 8 |
|  |  | 0 1 2 3 4 5 6 7 8 |
|  |  | 0 1 2 3 4 5 6 7 8 |
| ©2001 | NOT A SUBSTITUTE FOR A PHYSICIAN.<br>SEE A DERMATOLOGIST<br>FOR REGULAR CHECKUPS. |

FIG. 4

MOLE MONITORING SYSTEM

CROSS REFERENCE TO RELATED APPLICATIONS

Not Applicable

STATEMENT REGARDING FEDERALLY SPONSORED RESEARCH & DEVEL

Not Applicable

REFERENCE TO SEQUENCE LISTING

Not Applicable

BACKGROUND OF THE INVENTION

The present invention relates to methods for detecting and monitoring the growth and change in size, shape, color, "geography", and bleeding in moles, freckles and/or other pigmented skin lesions, which normally are visually unnoticed.

The present invention's classification pertains to the field of healthcare. Home healthcare, dermatology, as well as all areas of the medical field would either directly or indirectly be affected by its utilization.

With skin cancer and deadly melanoma on the rise and a large percentage of the population unaware of the warning signs of skin cancer, people need a product that can help educate them about the warning signs of skin cancer; and empower individuals by putting their dermatologic health literally "in their own hands". Having no way for people to compare a mole to what it looked like one of two years prior, people do not give much thought to their moles or freckles. They see no reason to make an appointment with a dermatologist—everything seems fine. People can't get treatment if they don't see a physician—they don't see a physician unless they notice they have a problem.

By the time the patient makes an appointment with a dermatologist, the lesion may be advanced and require extensive medical or surgical treatment. Sometimes, the disease is so advanced that it proves fatal. Patient awareness is the first step toward treatment and cure.

There are presently products on the market for checking moles. Some contain a measuring device which allows for a margin of error if not used carefully. Others are software related, expensive, high-tech, require photography, or are geared toward use by physicians only. These available products exclude people without technological expertise, of lesser educational backgrounds or of limited financial means, the elderly, non-english speaking people, nonmedical people, or anyone who shies away from using complex products—which could be most of the population!

Discovered during the patent search are patented products: #6155603 (Fox), #5727949 (Bar-Or), #5636873 (Sonsteby), #5992890 (Simcox), #5984685 (Portnoy), of which only a couple are somewhat relative to the present invention. All of these patented products differ from the present invention in either, composition, form or function and all are to be used only by medical, clinical or laboratory personnel—none are specifically designed for patient use.

BRIEF SUMMARY OF THE INVENTION

The present invention is a transparent flexible sheet onto which the size and shape of a pigmented skin lesion, mole or skin growth is recorded by laying the sheet over the lesion and tracing it in permanent pen onto the transparent sheet. The date of the tracing is also added to the sheet. The mole's color, geography or bleeding is also recorded by using the sheet's numeric feature, with a number representing each color or characteristic. The user circles the numbers representative of the physical characteristics of the traced mole. With a date, the size and shape, colors, geography or bleeding recorded, a method of comparison is created. By comparing subsequent recordings to the initial recording, the user is able to see even a minor change and make an appointment with a doctor. The user can bring the recording sheet to the dermatologist during the appointment, thus providing the physician with a history on the changing mole.

The present invention would allow anyone in the privacy of their own home to monitor changes in moles, freckles or other skin growths, notice a change, and make an appointment with a physician. The present invention is easy to use allowing people from all educational backgrounds to use it and understand the results. The present invention is inexpensive, easily stored, serves as a healthcare reminder, and can also serve as a historical reference tool for the physician during a patient's initial appointment.

The present invention is inexpensive to produce and would also be to purchase allowing for all income groups to benefit. The present invention is simple to use and lightweight—allowing for use by the elderly.

The present invention is nontechnical and nonmechanical—allowing for all educational groups to benefit.

The present invention can be used internationally by simply translating into the appropriate language.

The present invention can be used by multiple individuals. Every member in a household can use it.

The present invention can be used as a historical info tool for reference by a dermatologist during an initial visit. A dermatologist may measure a mole during a first visit and ask that the patient return for a followup to remeasure the mole. If the patient brings the present invention in when he first sees the dermatologist, the physician receives an immediate history about the changing lesion. Not only is the present invention a tool for the patient, it can double as an informational tool for the physician.

The present invention serves as a reminder for the user to see a dermatologist for regular checkups.

The present invention has the capability of monitoring a mole for longer than just one year, as it may take years for a normal mole to develop into a cancer.

The present invention is easily stored (like a box of bandages) in a medicine cabinet and would serve as a daily reminder to be used.

The present invention has an indefinite shelf life.

The present invention provides the user a means of noticing changes in the size, shape, color, geography or the presence of blood in a mole—all of which are warning signs to skin cancer and melanoma.

The present invention can help solve a major problem in treating and curing skin cancer and preventing death from melanoma . . . getting people to themselves notice a problem in the early stages and make an appointment with a dermatologist. Patient awareness is the first step to treatment and cure.

Other products on the market use measuring tools (a margin of error), computer software, photography, or digital imaging (expensive, complicated) or are used only by skilled medical professionals. They may exclude the most important person where healthcare is concerned - - - the individual. They are the ones that need to notice a problem then make the appointment. They can't be diagnosed, treated or cured if they don't make an appointment. The present invention is simplistic; can be used and understood by anyone; has an indefinite shelf life, and can be used internationally simply by printing it in the appropriate language. The present invention would be inexpensive allowing for use by all, and not excluding any one income group. Advances in technology would not negatively affect the present inventions need.

BRIEF DESCRIPTION OF THE SEVERAL VIEWS OF THE DRAWINGS

FIG. 1—view of a single mole monitoring system sheet, prior to use, according to the present invention.

FIG. 2—view of a single mole monitoring system sheet, after three uses, according to the present invention.

FIG. 4—a clean unmarked copy of a single mole monitoring system sheet, prior to use.

DETAILED DESCRIPTION OF THE INVENTION

Figure 3:
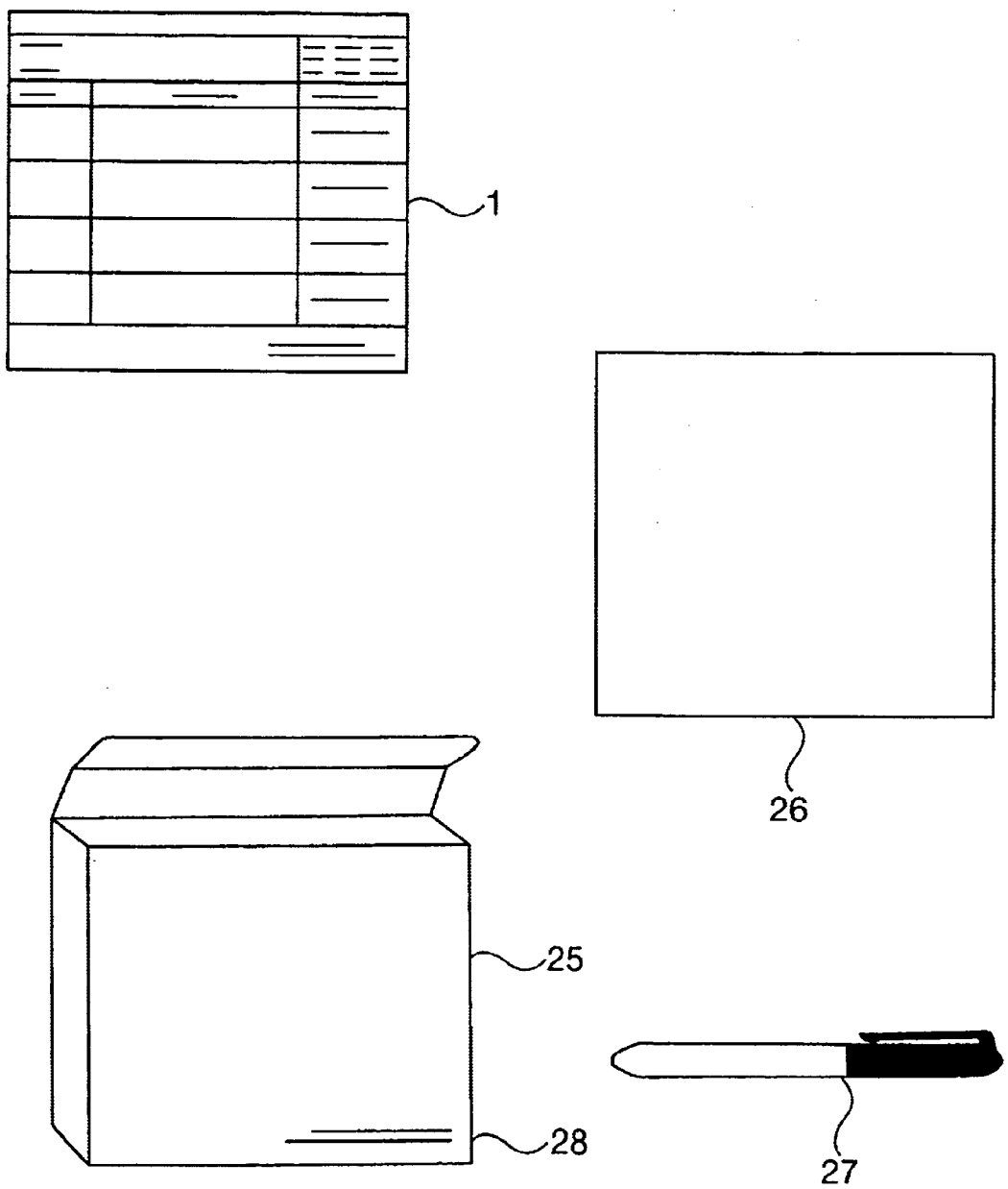
FIG. 3—view of all elements assembled, creating a kit, inclusive of the present invention.

There is a growing problem in the human population. It is an increasing incidence of skin cancer including deadly melanoma. Changes in the protective ozone layer, cumulative effects of years of sun exposure and tanning, prolonged exposure while using sunscreens that have had inadequate level of protection, and a lack of public knowledge about sun exposure, skin damage, and the warning signs of skin cancer are only a few reasons for the increase.

With the increase in skin cancer and melanoma, there is also an increase in healthcare costs, to the patient, insurance companies, and if a patient has no insurance, to the hospitals, the government (the taxpayers). Early diagnosis and early treatment of skin cancer is curative and less expensive; late diagnosis is costly, painful, and at times fatal. It is imperative we find ways to involve and educate the public to the early signs of skin cancer, melanoma and the changes in moles that signal serious disease, and give people a way to notice negative changes in their pigmented skin lesions. A patient needs to know they may have a problem in order to make an appointment with a physician. No appointment=No chance for early treatment or cure. Educating and empowering the patient is the best way to combat this increasing health threat.

The present invention consists of transparent, flexible sheets onto which a user records dates of the measures, the size and shape of a mole, color and geography (raised or flat) of a mole, and notes if any bleeding has occurred. Size and shape are recorded by using the transparent sheet as an overlay on the skin and permanently duplicating the mole details onto the sheet. The mole's color, bleeding and geography are recorded by using a numeric value system. The present invention is a means for someone to notice changes in a mole that previously would not have been noticed. People see their moles regularly, but only by comparisons can changes be noticed - - - the present invention both educates and empowers the individual by providing a simple comparison method.

Changes in color, size, shape, height and the appearance of blood are all characteristics that signal a problem, skin cancer, or melanoma. By using the present invention the user is also gaining knowledge about skin cancer and exactly what warning signs to look for. An involved, vigilant patient is the best defense against skin cancer and melanoma. The present invention's use helps to put dermatologic education, and vigilance literally "in a patient's hands".

The present invention is simple, lightweight, comprehensive, inexpensive, internationally usable, easily produced, nontechnical, nonmechanical, a personal reminder, quickly utilized, user-friendly, easily stored, an informative monitoring aid for patients and can provide physicians with early recorded patient information. All these features combined, create a product that people will use. The individual can be an important link in the fight against skin cancer and saving lives.

The most similar product presently on the market is a kit for measuring moles using a ruler-like measuring tool. Depending on how carefully the device is used, a margin of error could exist. People tend to shy away from using complex, mechanical or technical products—they may purchase it, but when it comes to using it, such a kit could remain unused.

Other related products on the market use computer software programs, photography or digital imaging, or are available only to skilled medical professionals. In these complex products, digital photos of a mole are taken, and with the use of flash digital photography and software programs, photos of moles can be compared to previous shots and viewed for comparison on a computer screen. There also exists lighted examination scopes for use only by medical professionals. Due to expense, technical/mechanical nature, camera or computer requirement, knowledge needed to use the equipment, or "medical professional only" availability, many population groups are excluded from using these currently available products.

Groups Excluded From Using Currently Available Products and Reasons

The elderly—many have no computer, no computer knowledge, lack dexterity to use cumbersome or intricate equipment, have limited income, may not remember to check their skin . . . they have chronic illnesses and many medications to remember to take. The elderly are often the ones who develop skin cancer from years of sun exposure.

The low income, lesser educated, or non-english speaking groups—their limited income, education, or the language barrier may not make computer, software, or camera ownership possible. There is a tendency for people with financial or educational limitations to overlook healthcare issues. They may put off physician appointment, or checkups until major symptoms occur. This could result in a late stage diagnosis and a possible negative treatment outcome. With products produced only in English, or no means for some individuals to know what products are available, or how to use them they also are excluded.

Anyone—who shies away from complicated systems, cumbersome equipment, costly products, anything that takes too much time to use, or any product that is not readily accessible, and potentially forgotten about. This group could be most of the population!

The present invention is a product that is such a simplistic form it is unlike any product presently on the market. The present invention does what other devices do, but in a user-friendly, simple form which can be used by literally anyone.

The present invention is inexpensive to produce. Materials needed for production are readily available through a printer. Since the present invention is not expensive to produce, it would be inexpensive to purchase. There is no technology or mechanical components to test or develop. All income level users can benefit.

The present invention is simple to use and lightweight allowing for use by the elderly.

The present invention is nontechnical and nonmechanical. Because the present invention does not use software, photography, nor require computer access, it has the potential to be used by all educational and age groups. Many people shy away from using complex products or anything that takes too much time to use. The present invention is simple to use and takes only a few moments to use, and will appeal to this group as well.

The present invention can be used in any country. By translating all of the information into the appropriate language it becomes a completely usable international product. The present inventions potential benefits are far reaching.

Because the present invention can be used by more than one person at a time, a whole family can benefit. If it is stored in a medicine cabinet, anyone who opens the cabinet will get a daily reminder to check their skin and moles.

The present invention can be used as a historical information tool for reference by a dermatologist during an initial visit. A dermatologist may measure a mole during a first visit and ask the patient to come back for a followup recheck at a later date. If the patient brings the present invention in when he first sees the dermatologist, the physician receives immediate historical information about the patient's changing mole. Not only is the present invention a tool for the patient, it can serve as an information history for the physician.

The present invention does not diagnose or treat an illness or disease, but provides a means for people to check their moles, and notice changes that would have normally gone unnoticed. The present invention serves as a reminder to see their dermatologist for regular checkups—a written reminder appears on the packaging and the individual transparent sheets. For the busy population, reminders have become very important—especially reminders to take care of their health.

The present invention has the capability of monitoring a mole or lesion for longer than just one year, as it may take years for a mole to develop into cancer. The present invention allows for 4 sequential measures for each mole. For example, if a mole is checked every 6 months—the present invention (an individual sheet) would be usable for 2 years. If the mole is checked once a year—the present invention (sheet) would be usable for 4 years.

The present invention is made from material having an indefinite shelf life and is easily stored in a medicine cabinet (like a box of bandages). These product features are very desirable to consumers/users.

The present invention provides the user a means of noticing changes in the size, shape, color, geography, or the presence of blood in a mole—all of which are warning signs to melanoma and other skin cancers. The present invention allows individuals to take a more active role in their healthcare, and at the same time educates them to the signs of disease and exactly what changes to look for in a mole.

The present invention can help solve a major problem in treating and curing skin cancer . . . getting people to themselves notice a problem in the early stages so they can make an appointment with a dermatologist. Patient awareness is the first step to prevention or cure. The Mole Monitoring System of this invention comprises.

The Mole Monitoring System Consists of 20 transparent, flexible sheets (the present invention) made from a transparent material to include plastic, polyester, vinyl, acetate, or a blended combination of materials to produce desired product. A suitable material could be acetate overhead transparency material. Each sheet size is apx. 4½ inches×4½ inches. Fixed information is imprinted on one side in black.

1 permanent thin tipped (for accuracy) black marker pen 4 cardboard cards, apx. size 4½×4½ inches, no imprinting, to be used to separate each users recording sheets within the storage box.

1 cardboard storage box, apx. size 5×5 inches, with 2 color printing, into which all components are assembled and provided.

Assembled kit stores accessibly in a medicine cabinet and could include information to the patient on cancer warning signs and changes to look for in moles.

The present invention is designed to use one single transparent sheet/per person/per mole and should be used in the following manner:

Referring to FIG. 2

The user takes a single transparent sheet (1) and the permanent marking pen (27). On the transparent sheet (1) under the "Name" heading (2), the user writes in marker, his name; (12) and under the "Location" heading (3) writes the physical location (13) of the mole or lesion being recorded. Examples of locations are "inside right thigh"; "left side neck"; or "right knee". Under the "Date" heading (4), the user adds in marker, in the first row (5) the date the mole is first recorded.

The user lays the transparent sheet (1) over the mole being recorded and with the permanent marker, under the "Tracing Area" heading (6) in the first row (5) duplicates the mole as viewed through the transparent sheet (1). With this step, the size and shape of the pigmented skin lesion is permanently recorded.

A reference key (7) for the number/characteristic values appears in the upper right corner of each transparent sheet (1). This key (7) should be used as a guide to determining which numbers accurately represent the mole's features.

The Reference Key (7) is Composed of the Following Information

Numbers 0 thru 5 identify lesion/mole color.
0=white, 1=tan, 2=red, 3=brown, 4=blue, 5=black
Numbers 6 and 7 denote lesion/mole geography.
6=flat, 7=raised
Number 8 denotes if lesion/mole is or has been bleeding.
8=blood The user removes the transparent sheet (1) from the skin surface. The user visually inspects the mole, and under the "Appearance" heading (8), in the first row (5) records the numeric value from the key (7) representing the physical characteristics of that mole by circling the appropriate numbers (9) with the permanent marking pen.

In FIG. 2, the user entered Jun. 15, 1999 as the date of the first measure (14) in the first row (5) on the transparent sheet (1). The mole was then duplicated (15) in detail by tracing it onto the sheet (1) in the first row (5) with the permanent marking pen. The mole's characteristics were recorded by circling the characteristic numbers (9) in the first row (5). The mole's first recording was tan (16) and flat (17). A baseline for comparison is now created. This initial recording is what all future recordings will be compared to.

The transparent sheet (1) is then filed in the box (25) for future use. The transparent sheets (1) can be grouped by user name within the box (25) by using the individual divider cards (26). Follow-up recordings can be done at any time, (ie, 3 months, 6 months, 1 year, etc). However a dermatologist should be consulted to determine how often moles should be checked. Each transparent sheet (1) can be used to record a mole 4 times.

In FIG. 2 the user entered Feb. 10, 2000 as the date of the second measure (18) in the second row on the transparent sheet (1). The mole was then duplicated (19) in detail by tracing it onto the sheet (1) in the second row. The mole's features are recorded by circling the characteristic numbers in the second row. The mole's second recording denotes a change from the earlier baseline recording. Although the mole is still tan and flat, the addition of a color red (20) is noted.

With 2 sequential mole recordings, the user can clearly see growth and change in the mole's shape as well as color changes. The user becomes aware of the need to see a dermatologist.

In FIG. 2, the user entered the date of Dec. 30, 2000 for the third recording (21) in the third row on the transparent sheet (1). The same mole was then duplicated (22) in detail by tracing it onto the sheet (1) in the third row. The mole's features were recorded by circling the characteristic numbers in the third row. The mole's third recording denotes many changes from the earlier baseline recording and from the second recording. In addition to still being tan and red, the mole is no longer flat but has become raised (24) and the color black (23) has appeared.

The user compares the mole recordings to the earliest baseline record and will visually notice any change in size, shape, the appearance of blood, and any change in elevation (geography). Any change at all in a mole's features requires a dermatologist appointment.

With 3 sequential mole recordings, the user can clearly see growth and changes in the shape of the mole. With the 3 sequential numeric recordings, there is a color change and a negative progression in the geography of the mole. There are significant changes when the third recordings are compared to the earliest baseline record. The user clearly sees a need to see a dermatologist.

If a mole is in a body location that is not easily accessible, another person can trace the mole or lesion. The present invention's flexibility allows for use on curved body surfaces.

The kit can be stored in a medicine cabinet and can serve as a daily reminder to be used regularly. There is also a reminder on each transparent sheet (1) and on the box (25) that this product is not a substitute for a physician and the user should see their dermatologist for regular checkups (10,28).

The patient can bring the transparent sheet (1) with the mole recordings to the dermatologist during a followup visit and can be used by the doctor as a source of historical information about a patients mole.

The incidence of skin cancer and melanoma is increasing drastically. The present invention can be a valuable tool for use by "everyday people" in the fight against these deadly but preventable diseases.

What is claimed is:

1. A method of monitoring pigmented skin lesions, the method comprising the steps of:

entering a date in a first region of multiple regions within a date section of a flexible sheet;

laying the flexible sheet over a region of skin so that a pigmented skin lesion within the region of skin is visible through a first transparent region of a plurality of transparent regions within a tracing section of the flexible sheet;

tracing a first outline of the pigmented skin lesion in the first transparent region within the tracing section of the flexible sheet, using an alphanumeric key associating multiple appearance characteristics of pigmented skin lesions to multiple codes, entering at least one code of the multiple codes associated with one or more appearance characteristics of the pigmented skin lesion on a first region of a plurality of regions within an appearance section of the flexible sheet;

after a time has lapsed in which the outline and/or the appearance characteristics of the pigmented skin lesion may have changed, entering a date in a second region of the multiple regions within the date section of the flexible sheet;

laying the flexible sheet over the pigmented skin lesion so that the pigmented skin lesion is visible through a second transparent region of the plurality of transparent regions within the tracing section of the flexible sheet;

tracing a second outline of the pigmented skin lesion in the second transparent region;

using the alphanumeric key, entering at least one code of the multiple codes associated with one or more appearance characteristics of the pigmented skin lesion on a second region of the regions within the appearance section of the flexible sheet; and comparing the second outline of the pigmented skin lesion in the second transparent region of the tracing section with the first outline of the pigmented skin lesion in the first transparent region of the tracing section, and comparing the at least one code entered in the second region of the appearance section with the at least one code entered in the first region of the appearance section.

2. A method according to claim 1, wherein at least one code is entered indicating color of the pigmented skin lesion.

3. A method according to claim 1, wherein at least one code is entered indicating geography of the pigmented skin lesion.

4. A method according to claim 1, wherein at least one code is entered indicating whether the pigmented skin lesion has bled.

5. A method according to claim 1, further comprising the step of using a second flexible sheet to trace and enter appearance characteristics of a second pigmented skin lesion.

6. A method according to claim 1, further comprising the step of recording physical location of the pigmented skin lesion on a fourth section of the flexible sheet.

7. A method according to claim 1, wherein a permanent marker is used to enter the date, trace the outline, and enter the at least one code.

8. A method according to claim 1, wherein the first and second transparent regions of the tracing section are adjacent each other so that the first and second outlines of the pigmented skin lesion are adjacent each other during the comparing step.

9. A method according to claim 1, further comprising the step of delivering the flexible sheet to medical personnel, wherein the first and second outlines of the pigmented skin lesion and the at least one code entered in the first and second regions of the appearance section provide a history of the pigmented skin lesion to the medical personnel.

* * * * *